(12) United States Patent
Kumar et al.

(10) Patent No.: US 10,070,868 B2
(45) Date of Patent: Sep. 11, 2018

(54) RESECTION SHIFT GUIDE AND METHOD

(71) Applicant: Zimmer, Inc., Warsaw, IN (US)

(72) Inventors: Harish Kumar, Warsaw, IN (US); Jason S. Toler, Pierceton, IN (US); Michael Boone, North Manchester, IN (US)

(73) Assignee: Zimmer, Inc., Warsaw, IN (US)

( * ) Notice: Subject to any disclaimer, the term of this patent is extended or adjusted under 35 U.S.C. 154(b) by 974 days.

(21) Appl. No.: 14/447,714

(22) Filed: Jul. 31, 2014

(65) Prior Publication Data

US 2015/0038975 A1      Feb. 5, 2015

Related U.S. Application Data

(60) Provisional application No. 61/861,776, filed on Aug. 2, 2013.

(51) Int. Cl.
     *A61B 17/56*      (2006.01)
     *A61B 17/15*      (2006.01)

(52) U.S. Cl.
     CPC ................... *A61B 17/155* (2013.01)

(58) Field of Classification Search
     CPC ..... A61B 17/1764; A61B 17/17; A61B 17/15; A61B 17/154; A61B 17/155; A61B 17/157; A61B 2017/0268
See application file for complete search history.

(56) References Cited

U.S. PATENT DOCUMENTS

| | | | |
|---|---|---|---|
| 4,703,751 A * | 11/1987 | Pohl | A61B 17/155 606/53 |
| 5,417,694 A | 5/1995 | Marik et al. | |
| 5,925,049 A * | 7/1999 | Gustilo | A61B 17/155 606/82 |
| 6,283,685 B1 | 9/2001 | Lemieux | |
| 7,115,133 B2 | 10/2006 | Plumet et al. | |
| 7,780,672 B2 | 8/2010 | Metzger et al. | |
| 7,887,544 B2 | 2/2011 | Tornier et al. | |
| 7,938,833 B2 | 5/2011 | Bastian | |
| 8,038,681 B2 | 10/2011 | Koenemann | |
| 8,075,566 B2 | 12/2011 | Canonaco | |
| 8,114,086 B2 | 2/2012 | Claypool et al. | |
| 8,506,570 B2 | 8/2013 | Colquhoun et al. | |
| 8,702,714 B2 | 4/2014 | Martin et al. | |

(Continued)

*Primary Examiner* — Matthew Lawson
(74) *Attorney, Agent, or Firm* — Schwegman Lundberg & Woessner, P.A.

(57) ABSTRACT

Resection shift guides and methods providing anterior, posterior, clockwise, or counterclockwise adjustment of a 4-in-1 cut guide along a planar resected surface of a femur are disclosed. A resection shift guide can include a base member and a block member. The base member can include first and second arms. The block member can include a first end, rotatably coupled with the first arm, a second end, rotatably coupled with the second arm, and at least three surfaces extending between the first and second ends. Each of the at least three surfaces can include two or more drill holes arranged differently than drill holes of the other surfaces. A method can include removing a 4-in-1 cut guide from two original femoral lumens, drilling two adjusted femoral lumens using a resection shift guide, removing the resection shift guides, and attaching the 4-in-1 cut guide to the two adjusted femoral lumens.

20 Claims, 14 Drawing Sheets

(56) References Cited

U.S. PATENT DOCUMENTS

| | | | |
|---|---|---|---|
| 2007/0073306 A1* | 3/2007 | Lakin | A61B 17/155 606/87 |
| 2007/0219559 A1* | 9/2007 | Heavener | A61B 17/1764 606/87 |
| 2007/0270877 A1 | 11/2007 | Park | |
| 2013/0012949 A1 | 1/2013 | Fallin et al. | |
| 2014/0005672 A1 | 1/2014 | Edwards et al. | |

* cited by examiner

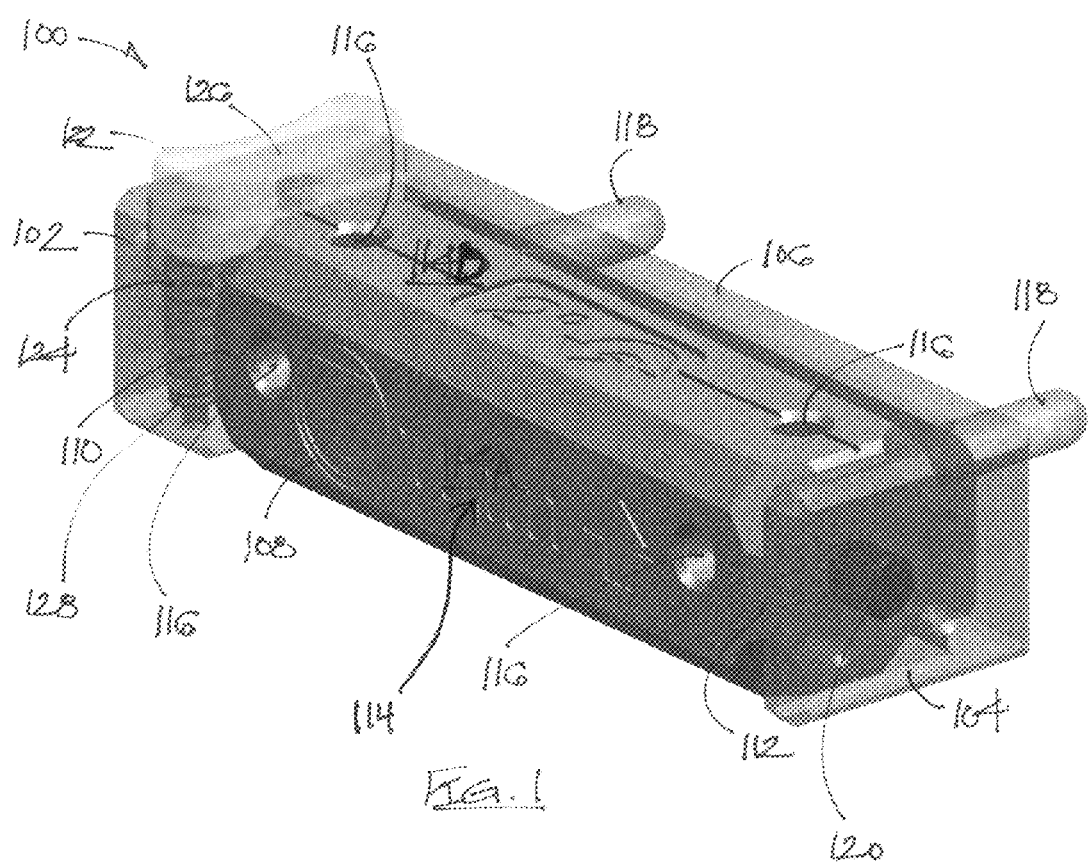

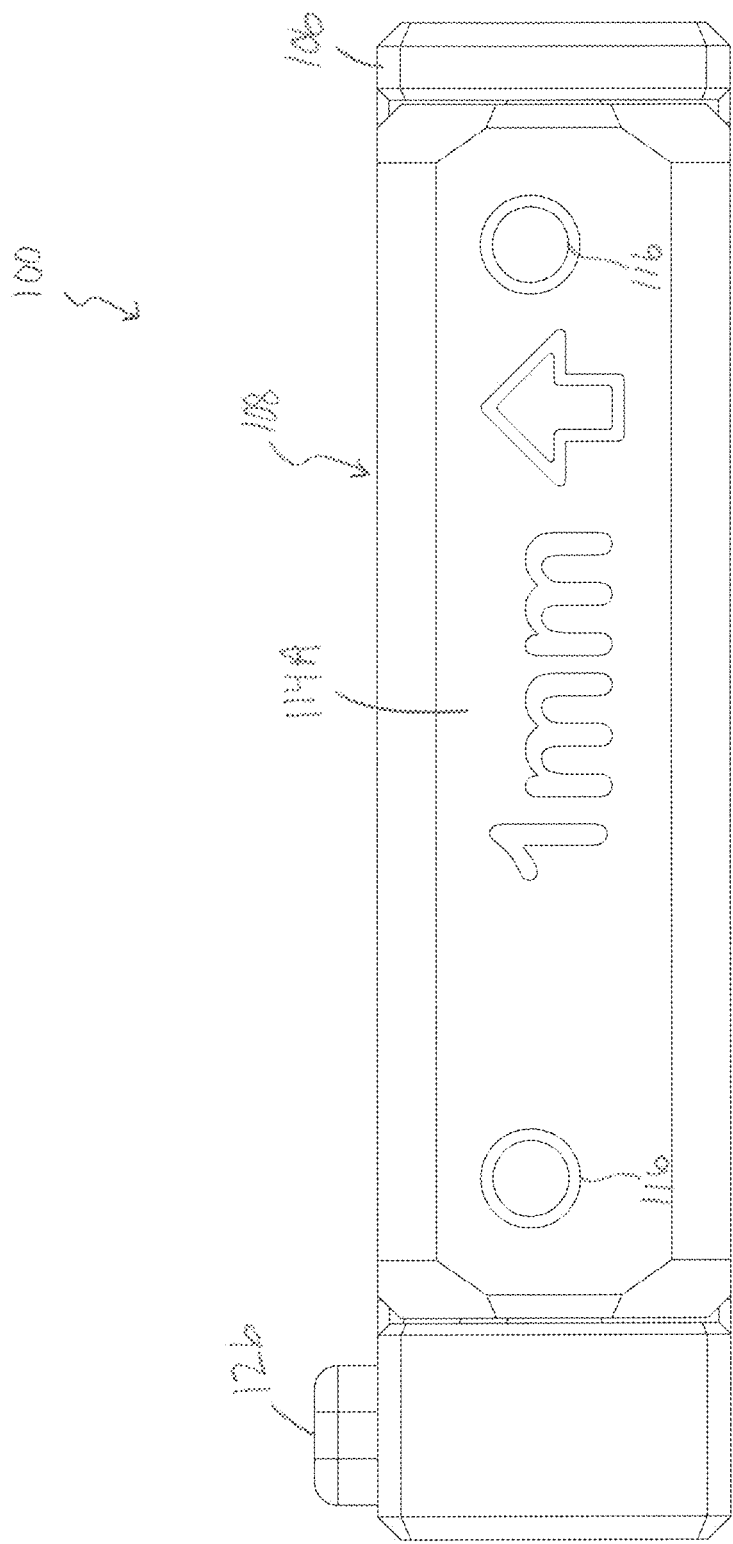

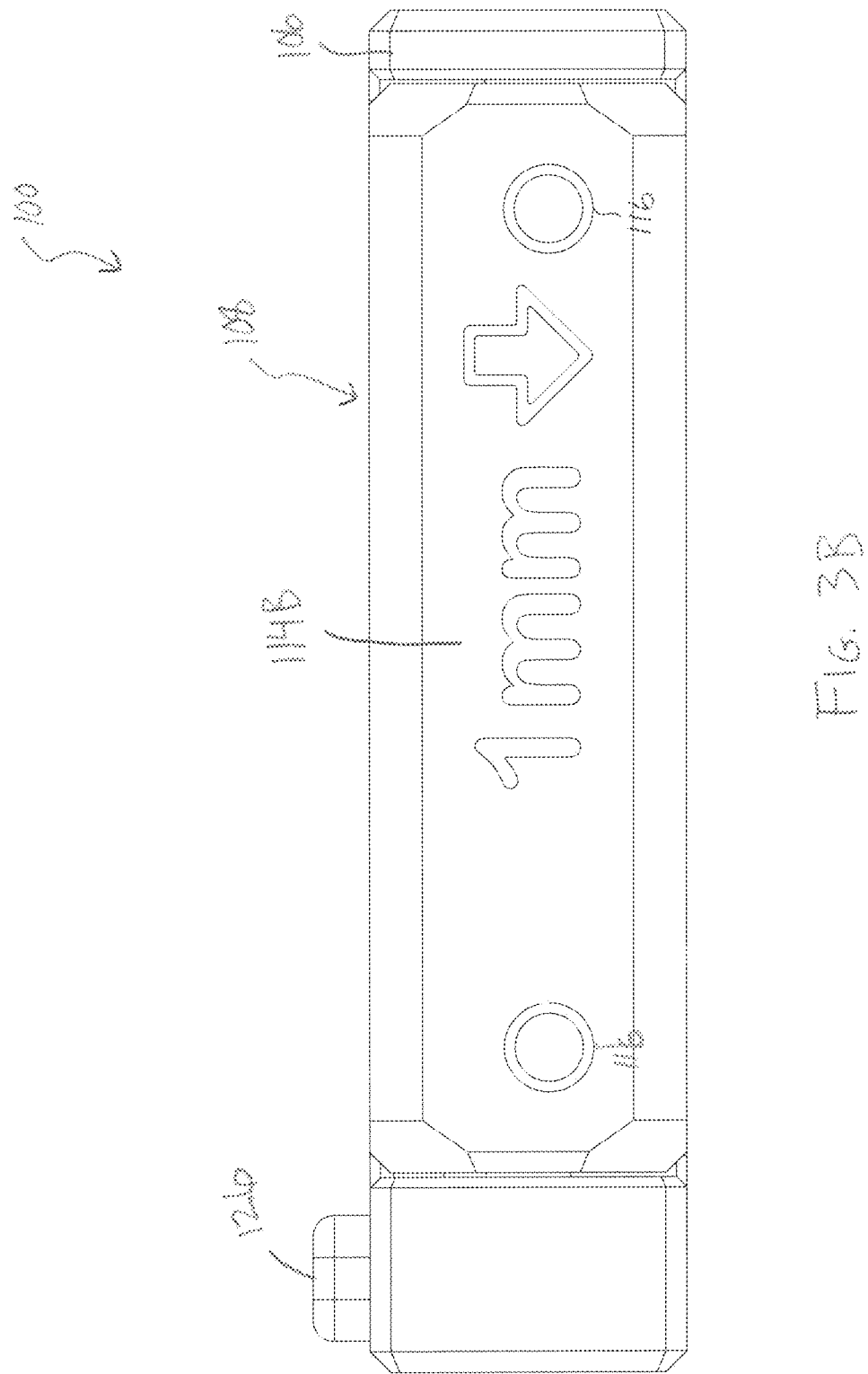

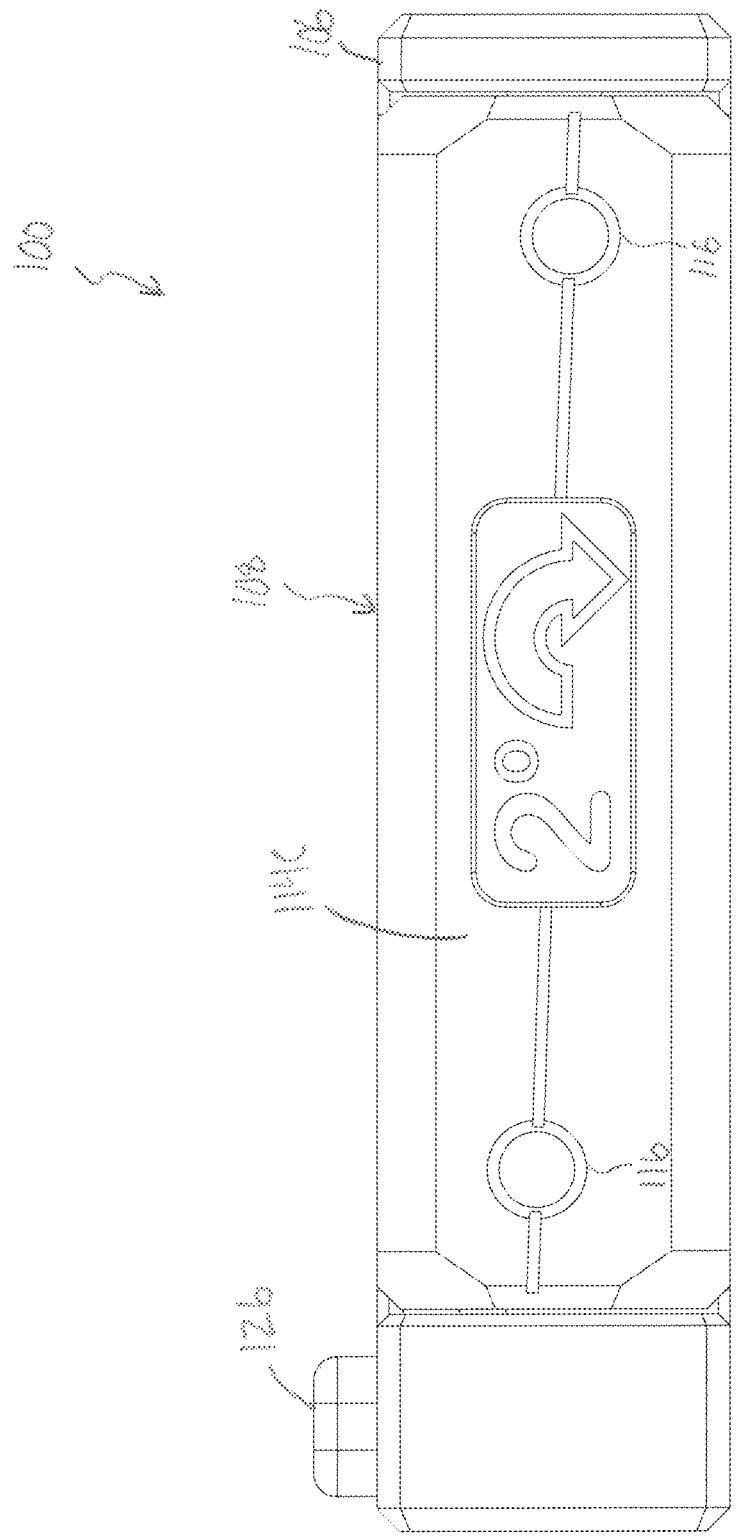

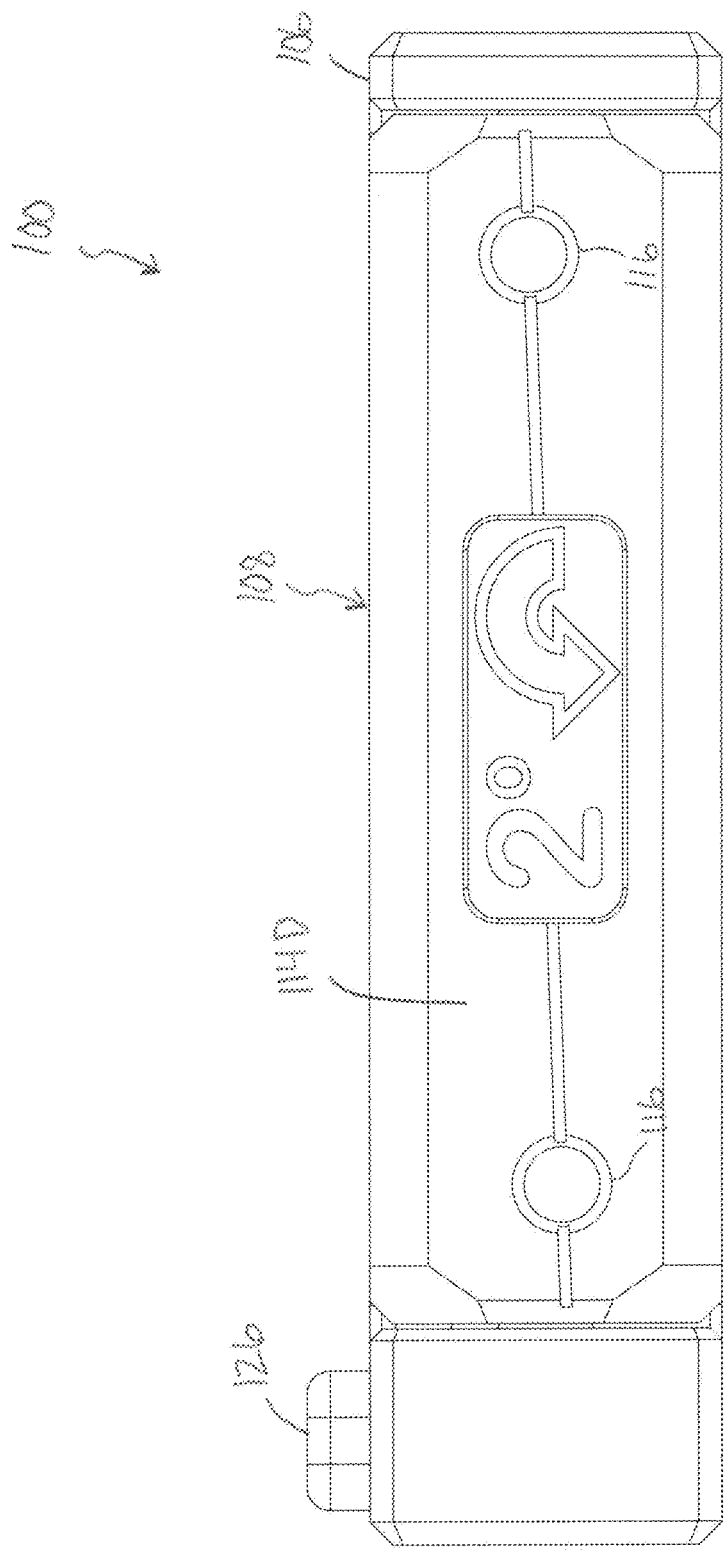

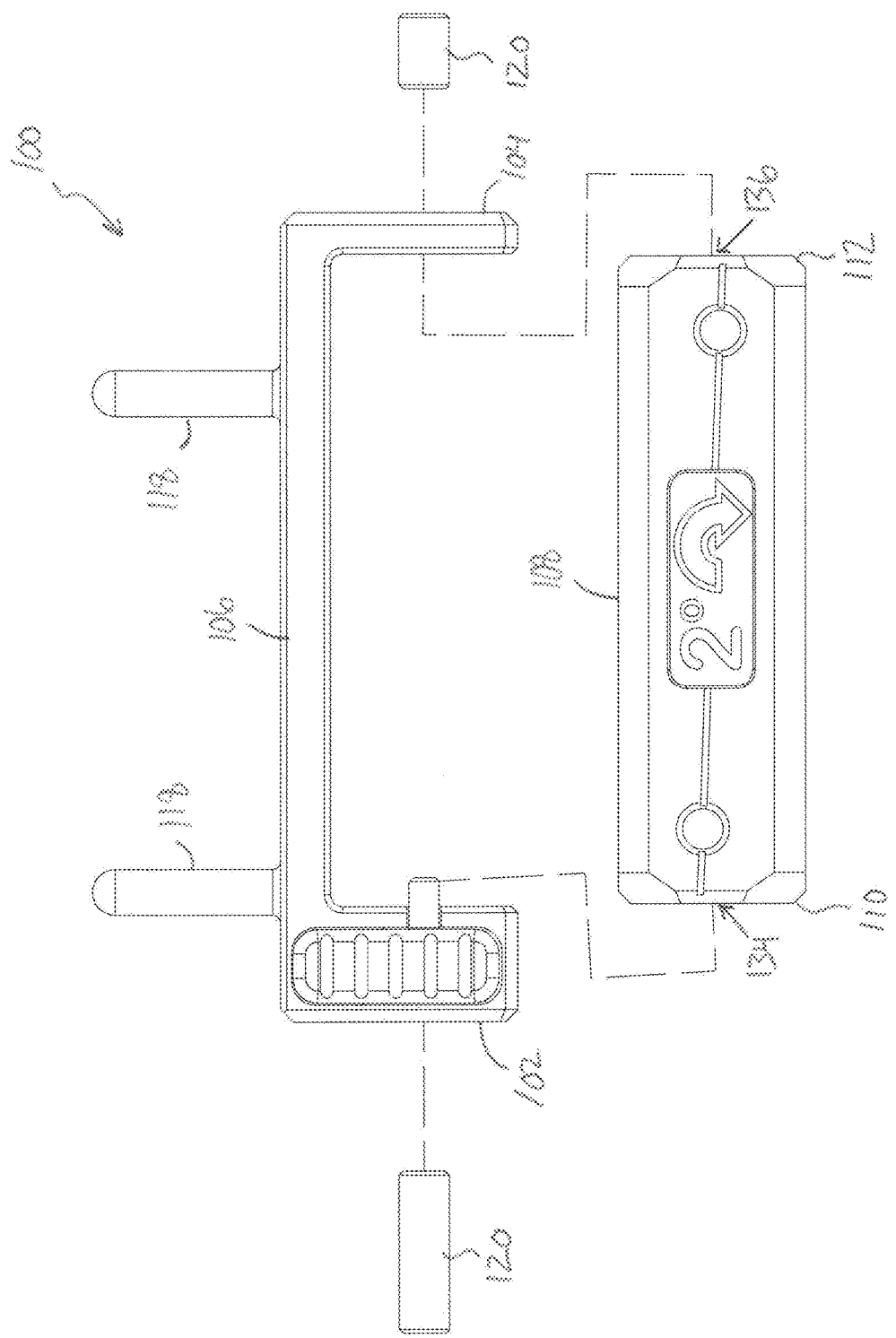

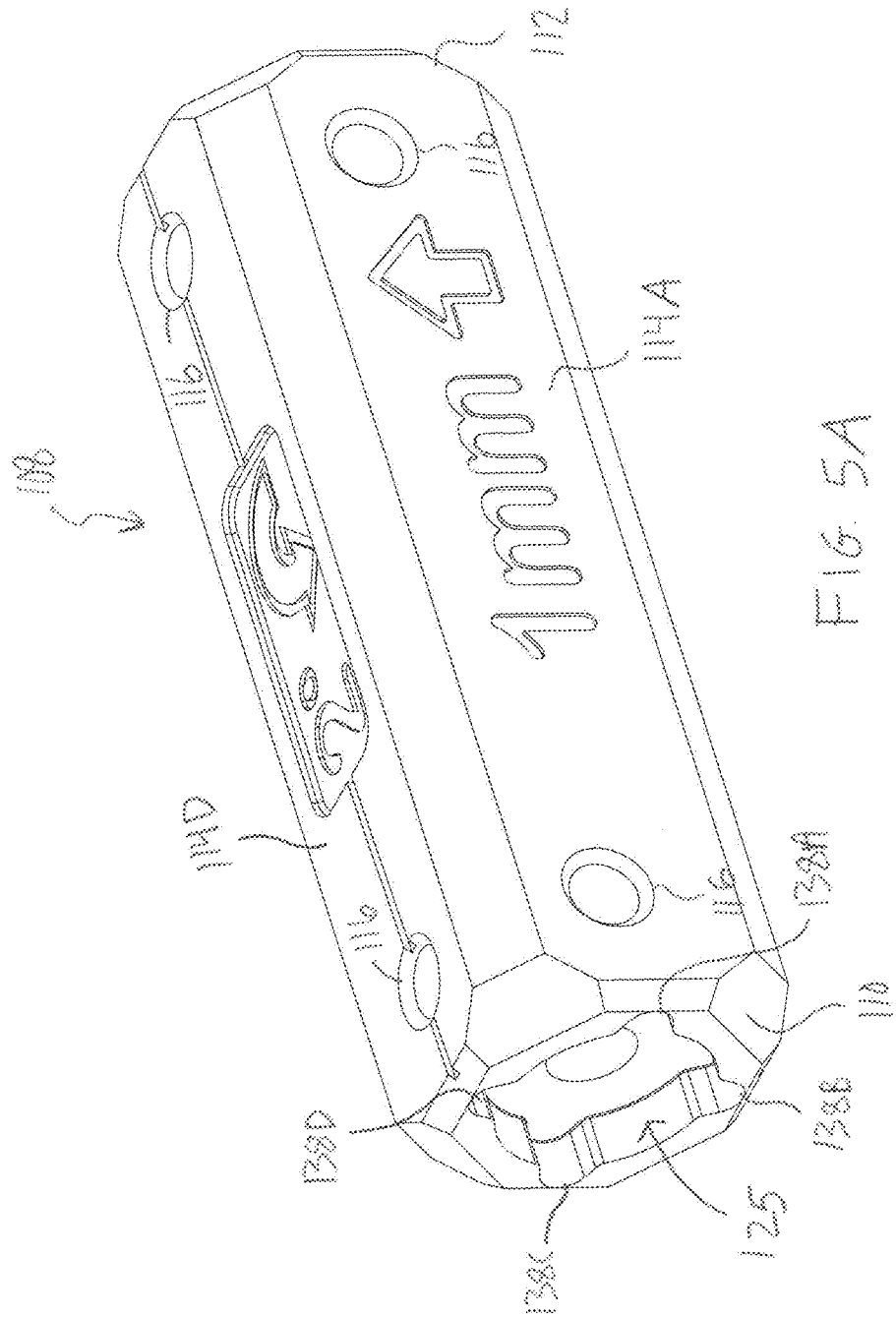

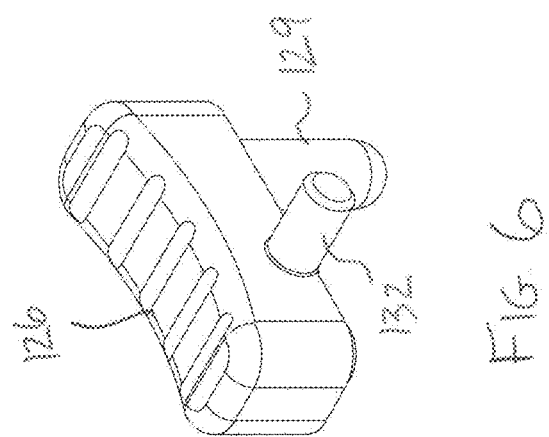

RESECTION SHIFT GUIDE AND METHOD

CLAIM OF PRIORITY

This application claims the benefit of U.S. Provisional Patent Application Ser. No. 61/861,776, filed on Aug. 2, 2013, the benefit of priority of which is claimed hereby, and which is incorporated by reference herein in its entirety.

TECHNICAL FIELD

This patent document pertains generally to resection devices and methods.

BACKGROUND

One or more guides can be used to appropriately resect a distal end of a femur. It can be desirable or necessary to adjust a first guide relative to the femur using a second guide.

After the resection has been completed, a prosthetic component can be secured to the resected femur.

OVERVIEW

In knee arthoroplasty procedures, a resection shift guide can allow a user (e.g., an orthopedic surgeon) to adjust a position of a 4-in-1 cut guide relative to a femoral plane prior to making various femoral resections.

The present inventors recognize, among other things, that existing resection shift guides do not allow for angular (e.g., clockwise or counterclockwise) and linear adjustments along a femoral resected plane to be made for a 4-in-1 cut guide. The present inventors further recognize that existing resection shift guides provide visual clutter and can inhibit a user's line of sight during a resection procedure.

Resection shift guides and methods providing anterior, posterior, clockwise, or counterclockwise adjustment of a 4-in-1 cut guide along a planar resected surface of a femur are disclosed in this patent document. A resection shift guide can include a base member and a block member. The base member can include first and second arms. The block member can include a first end, rotatably coupled with the first arm, a second end, rotatably coupled with the second arm, and at least three surfaces extending between the first and second ends. Each of the at least three surfaces can include two or more drill holes arranged differently than drill holes of the other surfaces. The differing drill hole combinations can provide different shifting or adjustment of the 4-in-1 cut guide along the planar resected surface.

A method can include removing a 4-in-1 cut guide from two original femoral lumens, configuring a resection shift guide to provide a desired shift along a resected planar surface, attaching the resection shift guide to the two original femoral lumens, drilling two adjusted femoral lumens using the resection shift guide, removing the resection shift guide from the two original femoral lumens, and attaching the 4-in-1 cut guide to the two adjusted femoral lumens.

To better illustrate the resection shift guide and related method disclosed herein, a non-limiting list of examples is provided here:

In Example 1, a resection shift guide can be provided that includes a base member including first and second arms, and a block member including a first end, rotatably coupled with the first arm, a second end, rotatably coupled with the second arm, and at least three surfaces extending between the first and second ends, each of the at least three surfaces including two or more drill holes arranged differently than drill holes of the other surfaces.

In Example 2, the resection shift guide of Example 1 is optionally configured to include first and second femoral posts longitudinally extending from the base member in a direction opposite the first and second arms.

In Example 3, the resection shift guide of any one of or any combination of Examples 1-2 is optionally configured to include a first axis pin, rotatably coupling the first end of the block member and the first arm of the base member, and a second axis pin, rotatably coupling the second end of the block member and the second arm of the base member.

In Example 4, the resection shift guide of any one of or any combination of Examples 1-3 is optionally configured to include a locking mechanism to rotationally lock a position of the block member relative to the base member.

In Example 5, the resection shift guide of Example 4 is optionally configured to include an actuating member that, when triggered, disables the locking mechanism and allows the block member to rotate relative to the base member.

In Example 6, the resection shift guide of Example 5 is optionally configured such that the actuating member includes a button and one or more resilient members biasing the button to an untriggered position.

In Example 7, the resection shift guide of Example 4 is optionally configured such that the locking mechanism includes one or more ball detents.

In Example 8, the resection shift guide of any one of or any combination of Examples 1-7 is optionally configured such that the block member includes four surfaces extending between its first and second ends.

In Example 9, the resection shift guide of Example 8 is optionally configured such that a first surface includes two or more drill holes arranged to provide an anterior shift, on a planar resected femur, to a subsequently installed 4-in-1 cut guide.

In Example 10, the resection shift guide of any one of or any combination of Examples 8-9 is optionally configured such that a second surface includes two or more drill holes arranged to provide a posterior shift, on a planar resected femur, to a subsequently installed 4-in-1 cut guide.

In Example 11, the resection shift guide of any one of or any combination of Examples 8-10 is optionally configured such that a third surface includes two or more drill holes arranged to provide a clockwise rotational shift, on a planar resected femur, to a subsequently installed 4-in-1 cut guide.

In Example 12, the resection shift guide of any one of or any combination of Examples 8-11 is optionally configured such that a fourth surface includes two or more drill holes arranged to provide a counterclockwise rotational shift, on a planar resected femur, to a subsequently installed 4-in-1 cut guide.

In Example 13, the resection shift guide of any one of or any combination of Examples 1-12 is optionally configured such that the two or more drill holes are spaced approximately 40 millimeters apart.

In Example 14, a method can include removing a 4-in-1 cut guide from two original lumens extending into a planar resected surface of a femur, configuring a resection shift guide to provide a desired shift to the 4-in-1 cut guide along the planar resected surface, including rotating a block member relative to a base member so that a surface of the block member including two drill holes, which provides the desired shift, extends orthogonally away from the planar resected surface, inserting first and second posts, extending from the base member of the resection shift guide, into the two original lumens, drilling through the two drill holes of the surface of the block member providing the desired shift, thereby forming two adjusted lumens extending into the planar resected surface, removing the resection shift guide from the two original lumens, and inserting the 4-in-1 cut guide into the two adjusted lumens.

In Example 15, the method of Example 14 is optionally configured to further include locking the block member relative to the base member when the surface of the block member, providing the desired shift, extends orthogonally away from the planar resected surface.

In Example 16, the method of Example 15 is optionally configured such that locking the block member relative to the base member includes allowing one or more resilient members to bias an actuating member to an untriggered position.

In Example 17, the method of any one of or any combination of Examples 14-16 is optionally configured such that configuring the resection shift guide includes arranging for an anterior shift of the 4-in-1 cut guide along the planar resected surface.

In Example 18, the method of any one of or any combination of Examples 14-16 is optionally configured such that configuring the resection shift guide includes arranging for a posterior shift of the 4-in-1 cut guide along the planar resected surface.

In Example 19, the method of any one of or any combination of Examples 14-16 is optionally configured such that configuring the resection shift guide includes arranging for a clockwise rotational shift of the 4-in-1 cut guide along the planar resected surface.

In Example 20, the method of any one of or any combination of Examples 14-16 is optionally configured such that configuring the resection shift guide includes arranging for a counterclockwise rotational shift of the 4-in-1 cut guide along the planar resected surface.

In Example 21, the resection shift guide or method of any one of or any combination of Examples 1-20 is optionally configured such that all elements or options recited are available to use or select from.

These and other examples and features of the present resection shift guide and method will be set forth in part in the following Detailed Description. This Overview is intended to provide non-limiting examples of the present subject matter—it is not intended to provide an exclusive or exhaustive explanation. The Detailed Description below is included to provide further information about the present resection shift guide and method.

BRIEF DESCRIPTION OF THE DRAWINGS

In the drawings, like numerals can be used to describe similar elements throughout the several views. The drawings illustrate generally, by way of example, but not by way of limitation, various embodiments discussed in the present document.

FIG. 1 illustrates an isometric view of a resection shift guide, in accordance with at least one example of the present disclosure.

FIG. 3A illustrates a first surface of a rotatable block member, in accordance with at least one example of the present disclosure.

FIG. 3B illustrates a second surface of the rotatable block member, in accordance with at least one example of the present disclosure.

FIG. 3C illustrates a third surface of the rotatable block member, in accordance with at least one example of the present disclosure.

FIG. 3D illustrates a fourth surface of the rotatable block member, in accordance with at least one example of the present disclosure.

FIG. 4 illustrates an exploded top view of the resection shift guide, in accordance with at least one example of the present disclosure.

FIG. 5A illustrates a perspective view of the rotatable block member, in accordance with at least one example of the present disclosure.

FIG. 6 illustrates a perspective view of a locking mechanism button, in accordance with at least one example of the present disclosure.

DETAILED DESCRIPTION

The present inventors recognize that a mechanized resection shift block providing linear and angular adjustments for a femoral cutting guide and for use during a knee arthoroplasty procedure can be beneficial. The resection shift block can allow a user to adjust the position of a femoral 4-in-1 cut guide prior to making various femoral resections. For example, if there is a chance of a notch occurring during a femoral anterior cut, the resection shift block can be used to shift the 4-in-1 cut guide holes anteriorly.

Figure 2A:
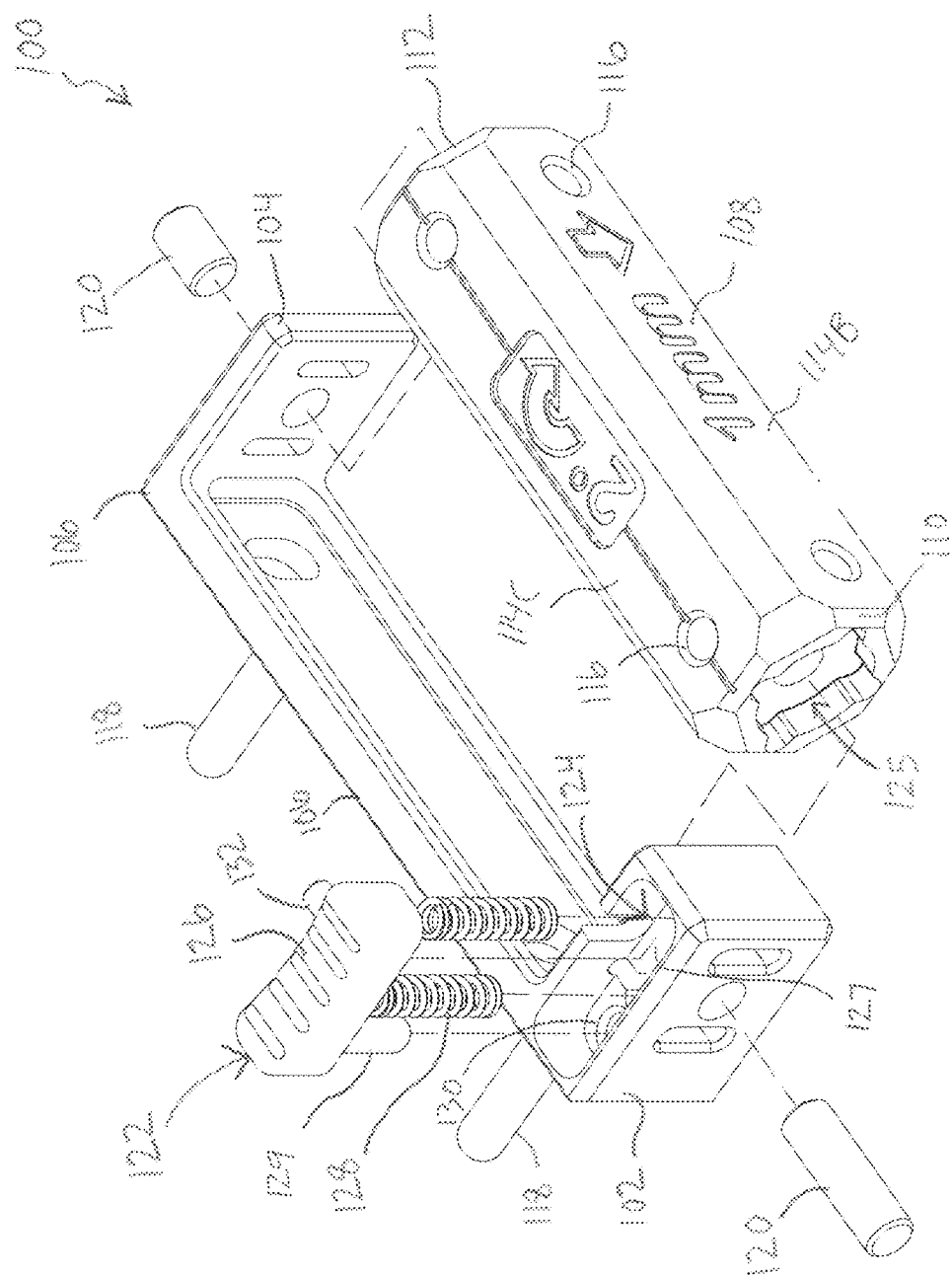
FIG. 2A illustrates an exploded perspective view of the resection shift guide, in accordance with at least one example of the present disclosure.
Figure 2B:
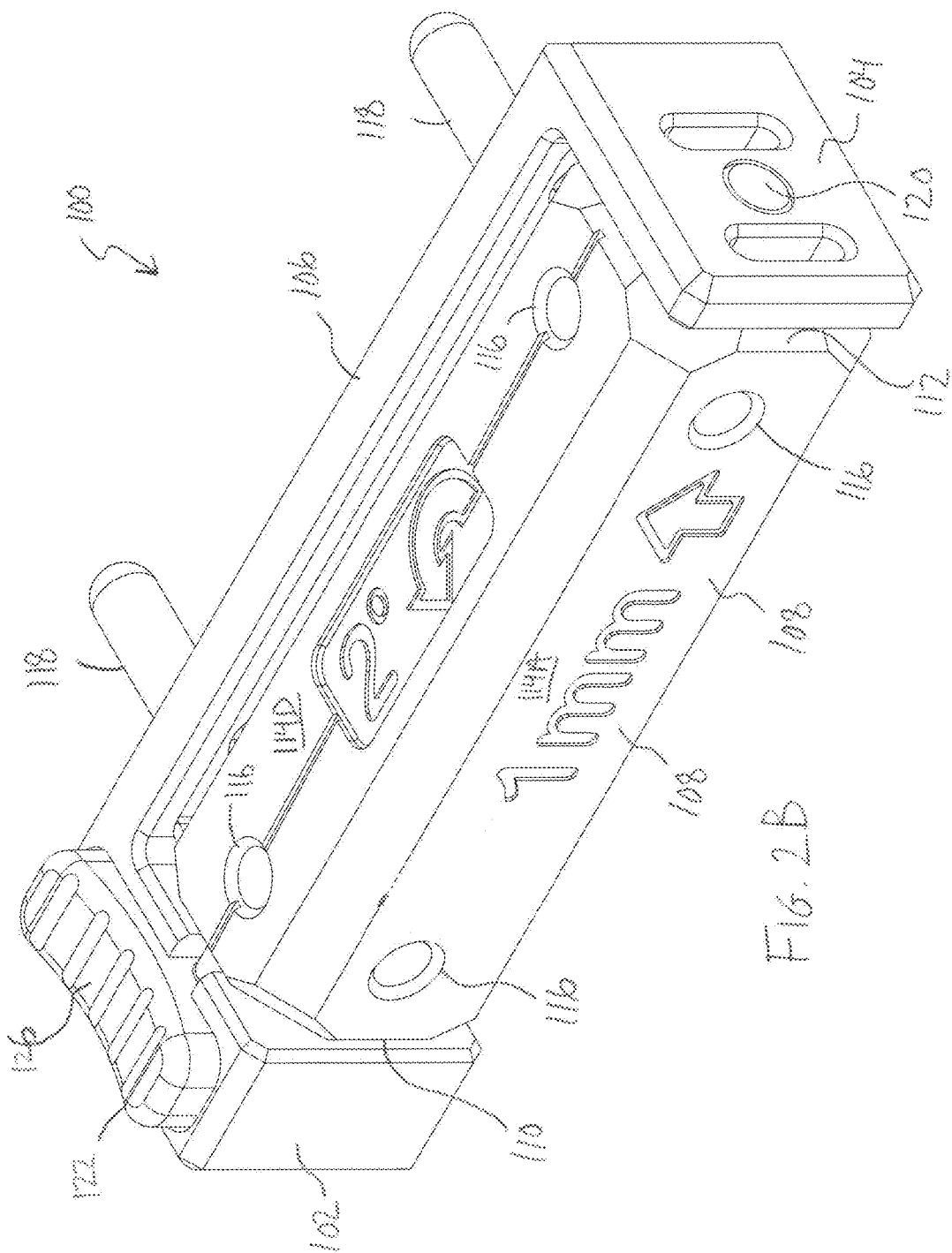
FIG. 2B illustrates another perspective view of the assembled resection shift guide, in accordance with at least one example of the present disclosure.
Figure 2C:
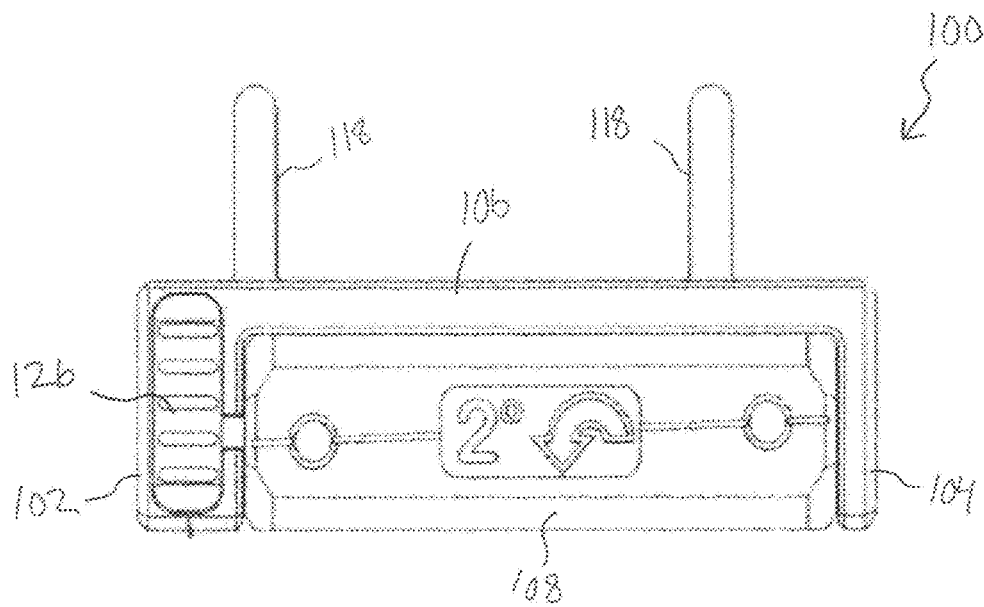
FIG. 2C illustrates a top view of the resection shift guide, in accordance with at least one example of the present disclosure.
Figure 2D:
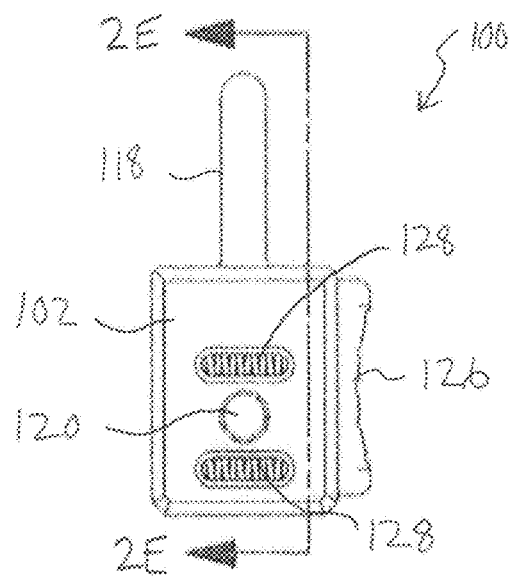
FIG. 2D illustrates a first side view of the resection shift guide, in accordance with at least one example of the present disclosure.
Figure 2E:
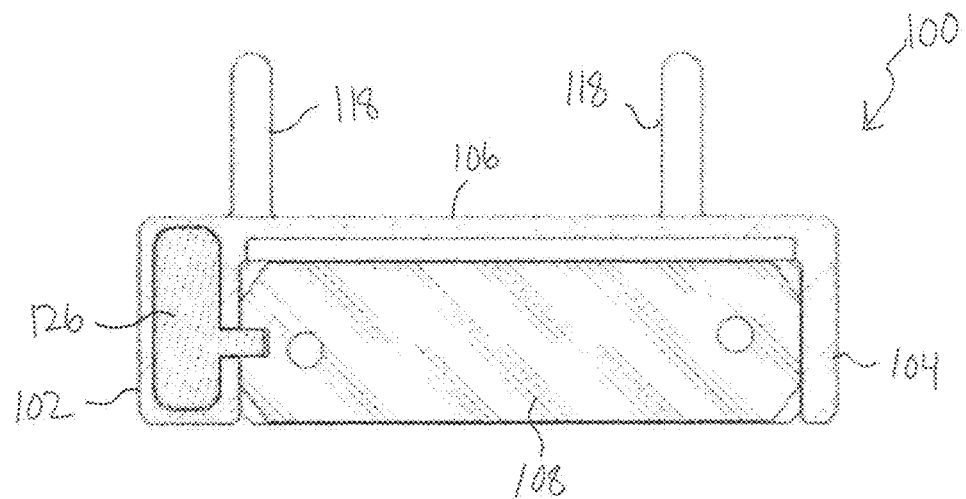
FIG. 2E illustrates a cross-sectional view of the resection shift guide taken along line 2E-2E in FIG. 2D, in accordance with at least one example of the present disclosure.
Figure 2F:
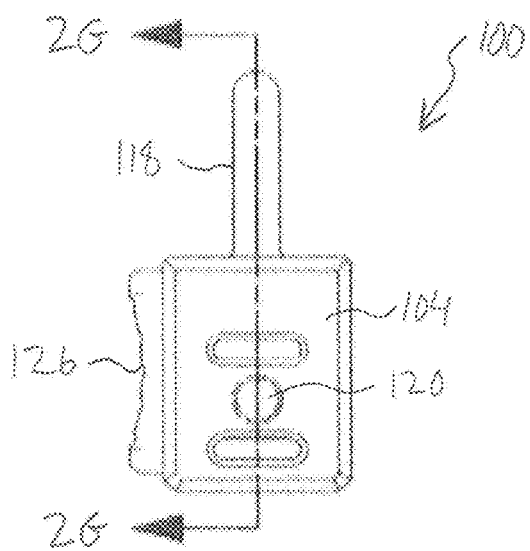
FIG. 2F illustrates a second side view of the resection shift guide, in accordance with at least one example of the present disclosure.
Figure 2G:
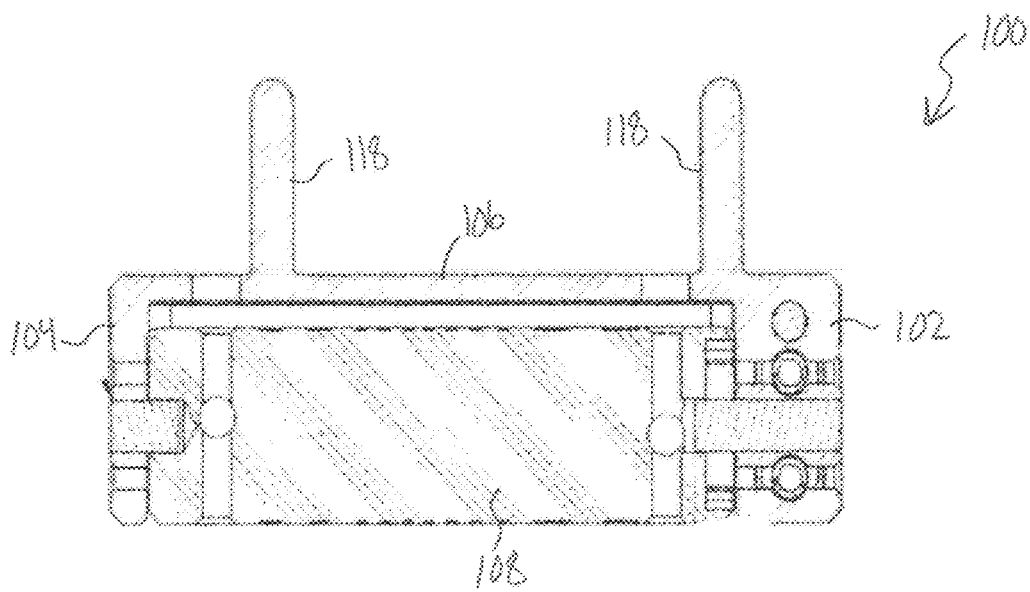
FIG. 2G illustrates a cross-sectional view of the resection shift guide taken along line 2G-2G in FIG. 2F, in accordance with at least one example of the present disclosure.
Figure 2H:
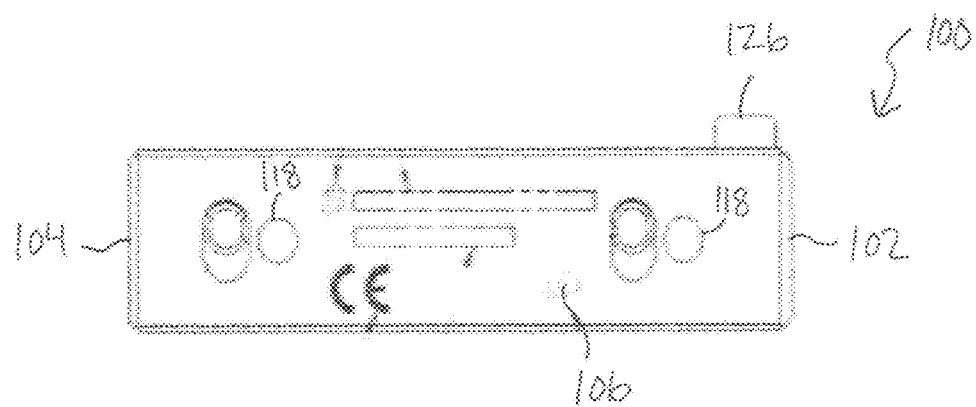
FIG. 2H illustrates a rear view of the resection shift guide, in accordance with at least one example of the present disclosure.

FIGS. 1 and 2A illustrate perspective and exploded perspective views, respectively of a resection shift guide 100 in accordance with at least one example of the present disclosure. The perspective view of FIG. 1 includes portions that are partially transparent to illustrate internal components of the resection shift guide 100. Furthermore, FIG. 2B illustrates another perspective view of the assembled resection shift guide 100; FIG. 2C illustrates a top view of the resection shift guide 100; FIG. 2D illustrates a first side view of the resection shift guide 100; FIG. 2E illustrates a cross-sectional view of the resection shift guide 100 taken along line 2E-2E of FIG. 2D; FIG. 2F illustrates a second side view of the resection shift guide 100; FIG. 2G illustrates a cross-sectional view of the resection shift guide 100 taken along line 2G-2G of FIG. 2F; and FIG. 2H illustrates a rear view of the resection shift guide 100.

The resection shift guide 100 can comprise a base member 106 and a block member 108. The base member 106 and the block member 108 can be formed from any suitable materials, including biocompatible metals and/or plastics. The base member 106 can include first and second arms 102, 104. The block member 108 can include a first end 110, rotatably coupled with the first arm 102, a second end 112, rotatably coupled with the second arm 104, and at least three surfaces 114 (e.g., 114A-D) extending between the first and second ends 110, 112. Rotational coupling between the block member 108 and the base member 106 can include first and second axis pins 120.

In the example shown, the resection shift guide 100 includes four surfaces 114 and is securable to a resected femur by at least first and second femoral posts 118. The femoral posts 118 longitudinally extend from the base member 106 in a direction opposite the first and second arms 102, 104. The compact nature of the resection shift guide 100 can advantageously reduce visual clutter and can provide good lines of sight to a user during a knee arthoroplasty procedure.

A locking mechanism 124 can be incorporated into one or both of the first and second arms 102, 104 to rotationally lock a position of the block member 108 relative to the base member 106. The locking mechanism 124 can include an axially symmetric pocket 125 with a plurality of peaks, such as four peaks corresponding to the four surfaces 114 of the block member 108. The axially symmetric pocket 125 can be formed from any suitable manufacturing method, such as milling.

An actuating member 122, when triggered (e.g., depressed), can disable the locking mechanism 124. Disabling the locking mechanism can allow the block member 108 to freely rotate relative to the base member 106. In an example, the actuating member 122 can include a button 126, one or more resilient members 128 configured to be positioned within a cavity 127 in the first arm 102 of the base member 106, and a guide post 129 configured to be slidable within a corresponding guide channel 130 in the first arm 102. The one or more resilient members 128 can bias the button 126 to an untriggered position in which a pin 132 is pushed into one of the four peaks of the axially symmetric pocket 125, thereby locking the block member 108 relative to the base member 106. Conversely, when the button 126 is depressed, the pin 132 can clear the peaks and the block member 108 can rotate freely until the button 126 is released.

In another example, the actuating member 122, when triggered (e.g., depressed), can enable the locking mechanism 124. Thus, when the button 126 is depressed, the pin 132 can engage one of the peaks in the axially symmetric pocket 125, thereby preventing the block member 108 from rotating relative to the base member 106. A suitable retention feature can be used to maintain the button 126 in a depressed state. When the retention feature is released, the button 126 can be pushed by the one or more resilient members 128 to the untriggered position, thereby allowing the block member 108 to rotate freely relative to the base member 106.

Alternatively or additionally, the locking mechanism 124 can include one or more ball detents that allow the block member 108 to be moved or "clicked" into place and engage the first and second arms 102, 104 of the base member 106. In an example, the one or more ball detents can hold or "lock" the block member 108 in place without the need for an "active" locking mechanism with a spring-loaded button, as described above.

Each of the at least three surfaces 114 can include two or more drill holes 116 arranged different than drill holes of the other surfaces. For example, each of four surfaces 114 can include two drill holes 116 providing one of four linear or rotational shift options—1 millimeter anterior shift as illustrated by surface 114A in FIG. 3A, 1 millimeter posterior shift as illustrated by surface 114B in FIG. 3B, 2 degree clockwise shift as illustrated by surface 114C in FIG. 3C, and 2 degree counterclockwise shift as illustrated by surface 114D in FIG. 3D—for a subsequently installed 4-in-1 cut guide on a planar resected femur. In other examples, the surfaces can provide for anterior and posterior shifts greater than or less than 1 millimeter. Similarly, the surfaces can provide for clockwise and counterclockwise shifts greater than or less than 2 degrees. The drill holes 116 can be spaced 40 millimeters apart to match the post spacing of the subsequently installed 4-in-1 cut guide. However, other drill hole spacings are also contemplated.

FIG. 4 is an exploded top view of the resection shift guide 100 illustrating how the block member 108 can be rotatably coupled to the base member 106, in accordance with at least one example of the present disclosure. As shown in FIG. 4, the first axis pin 120 can be inserted through an aperture (not shown) in the first arm 102 and can engage a first recess 134 at the first end 110 of the block member 108. Similarly, the second axis pin 120 can be inserted through an aperture (not shown) in the second arm 104 and can engage a second recess 136 at the second end 112 of the block member 108.

Figure 5B:
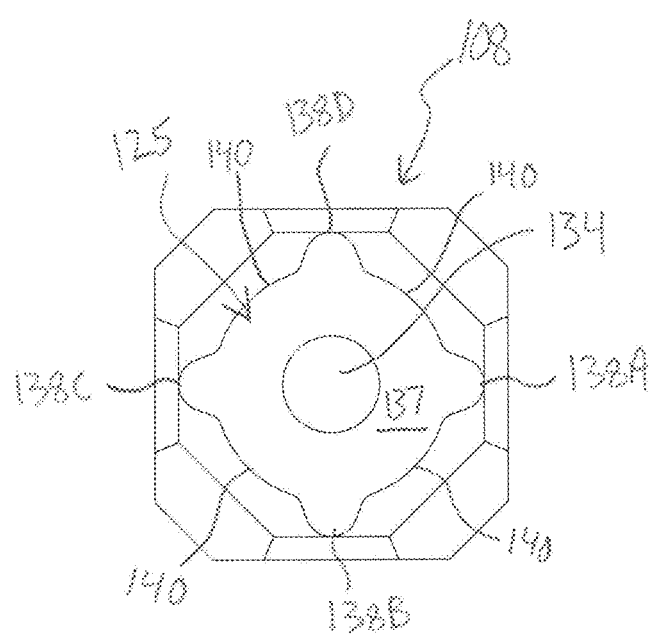
FIG. 5B illustrates an end view of the rotatable block member, in accordance with at least one example of the present disclosure.

FIGS. 5A and 5B are perspective and end views, respectively, of the block member 108 in accordance with at least one example of the present disclosure. As shown in FIGS. 5A and 5B, the axial symmetric pocket 125 can include a recessed center region 137 and four peaks 138A-D corresponding to the four surfaces 114A-D. As will be appreciated, the number of peaks 138 can correspond to the number of surfaces 114 on the block member 108. Thus, a three-sided block member can include three peaks, a five sided block member can included five peaks, and so forth.

A perspective view of the button 126 is illustrated in FIG. 6. With reference to FIGS. 5A, 5B, and 6, when the button 126 is depressed, the pin 132 can travel to the recessed center region 137 to avoid contact with any of the peaks 138 and allow the block member 108 to rotate freely. In an example, the pin 132 moves just far enough out of the peak 138 to allow it to ride along an inner surface 140 positioned between each adjacent peak 138 while the block member 108 is being rotated. When the user has rotated the block member 108 by an amount sufficient to select the desired surface 114, the button 126 can be released. Upon release of the button 126, the pin 132 will engage the peak 138 corresponding to the selected one of the surfaces 114.

A surgical method including use of the present resection shift guide can comprise the following steps:

(1) Removing a 4-in-1 cut guide (or other cut guide) from two original lumens extending onto a planar resected surface of a femur;

(2) Configuring the resection shift guide to provide a desired shift to the 4-in-1 cut guide along the planar resected surface. This can include rotating a block member relative to a base member so that a surface of the block member including two drill holes, which provides the desired shift, extends orthogonally away from the planar resected surface;

(3) Inserting first and second posts of the resection shift guide into the two original lumens;

(4) Drilling through the two drill holes of the surface of the block member providing the desired shift, thereby forming two adjusted lumens extending into the planar resected surface;

(5) Removing the resection shift guide from the two original lumens; and (6) Inserting the 4-in-1 cut guide into the two adjusted lumens.

Optionally, the method can further include locking the block member relative to the base member when the surface of the block member, which provides the desired shift, extends orthogonally away from the planar resected surface.

The above Detailed Description includes references to the accompanying drawings, which form a part of the Detailed Description. The drawings show, by way of illustration, specific embodiments in which the present resection shift block and method can be practiced. These embodiments are also referred to herein as "examples." While the Detailed Description focuses on use of the resection shift block and method with a knee arthoroplasty procedure, similar embodiments for use with other orthopedic non-knee joint procedures are also envisioned.

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, "anterior" refers to a direction generally toward the front of a patient, "posterior" refers to a direction generally toward the back of the patient, "medial" refers to a direction generally toward the middle of the patient, and "lateral" refers to a direction generally toward the side of the patient.

In the appended claims, the terms "including" and "in which" are used as the plain-English equivalents of the respective terms "comprising" and "wherein." The terms "including" and "comprising" are open-ended, that is, a system, kit, or method that includes elements in addition to those listed after such a term in a claim are still deemed to fall within the scope of that claim. Also, in the following claims, the "kit" claims are intended to provide protection for, among other things, a set novel shim components, at least one of which includes differing heights, and sensor, bearing support, and handling instrument components having a functional relationship with the novel shim components. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A resection shift guide, comprising:
   a base member including first and second arms; and
   a block member including a first end, rotatably coupled with the first arm, a second end, rotatably coupled with the second arm, and at least three surfaces extending between the first and second ends,
   each of the at least three surfaces including two or more drill holes arranged differently than drill holes of the other surfaces,
   the block member being rotatable about a longitudinal axis extending between the first and second arms of the base member while the first and second ends of the block member remain coupled to the respective first and second arms of the base member.

2. The resection shift guide of claim 1, further comprising first and second femoral posts longitudinally extending from the base member in a direction opposite the first and second arms.

3. The resection shift guide of claim 2, further comprising a first axis pin, rotatably coupling the first end of the block member and the first arm of the base member, and a second axis pin, rotatably coupling the second end of the block member and the second arm of the base member.

4. The resection shift guide of claim 3, further comprising a detent mechanism to rotationally lock a position of the block member relative to the base member.

5. The resection shift guide of claim 4, further comprising an actuating member that, when triggered, disables the detent mechanism and allows the block member to rotate relative to the base member.

6. The resection shift guide of claim 5, wherein the actuating member includes a button and one or more resilient members biasing the button to an untriggered position.

7. The resection shift guide of claim 4, wherein the detent mechanism includes one or more ball detents.

8. The resection shift guide of claim 1, wherein the block member includes four surfaces extending between its first and second ends.

9. The resection shift guide of claim 8, wherein a first surface includes two or more drill holes arranged to provide an anterior shift, on a planar resected femur, to a subsequently installed 4-in-1 cut guide.

10. The resection shift guide of claim 8, wherein a second surface includes two or more drill holes arranged to provide a posterior shift, on a planar resected femur, to a subsequently installed 4-in-1 cut guide.

11. The resection shift guide of claim 8, wherein a third surface includes two or more drill holes arranged to provide a clockwise rotational shift, on a planar resected femur, to a subsequently installed 4-in-1 cut guide.

12. The resection shift guide of claim 8, wherein a fourth surface includes two or more drill holes arranged to provide a counterclockwise rotational shift, on a planar resected femur, to a subsequently installed 4-in-1 cut guide.

13. The resection shift guide of claim 1, wherein the two or more drill holes are spaced approximately 40 millimeters apart.

14. A resection shift guide, comprising:
    a base member including first and second arms;
    first and second femoral posts longitudinally extending from the base member in a direction opposite the first and second arms; and
    a block member including a first end, rotatably coupled with the first arm, a second end, rotatably coupled with the second arm, and at least three surfaces extending between the first and second ends, each of the at least three surfaces including two or more drill holes arranged differently than drill holes of the other surfaces.

15. A resection shift guide, comprising:

a base member including first and second arms;

a block member including a first end, rotatably coupled with the first arm, a second end, rotatably coupled with the second arm, and at least three surfaces extending between the first and second ends, each of the at least three surfaces including two or more drill holes arranged differently than drill holes of the other surfaces;

a first axis pin, rotatably coupling the first end of the block member and the first arm of the base member; and a second axis pin, rotatably coupling the second end of the block member and the second arm of the base member.

16. The resection shift guide of claim 15, further comprising a detent mechanism to rotationally lock a position of the block member relative to the base member.

17. The resection shift guide of claim 15, wherein one of the surfaces includes two or more drill holes arranged to provide an anterior shift, on a planar resected femur, to a subsequently installed 4-in-1 cut guide.

18. The resection shift guide of claim 15, wherein one of the surfaces includes two or more drill holes arranged to provide a posterior shift, on a planar resected femur, to a subsequently installed 4-in-1 cut guide.

19. The resection shift guide of claim 15, wherein one of the surfaces includes two or more drill holes arranged to provide a clockwise rotational shift, on a planar resected femur, to a subsequently installed 4-in-1 cut guide.

20. The resection shift guide of claim 15, wherein one of the surfaces includes two or more drill holes arranged to provide a counterclockwise rotational shift, on a planar resected femur, to a subsequently installed 4-in-1 cut guide.

* * * * *